United States Patent
Lai et al.

(10) Patent No.: US 7,632,876 B2
(45) Date of Patent: Dec. 15, 2009

(54) POLYSILOXANE PREPOLYMERS FOR BIOMEDICAL DEVICES

(75) Inventors: Yu-Chin Lai, Pittsford, NY (US); Weihong Lang, Amston, CT (US); Edmond T. Quinn, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 338 days.

(21) Appl. No.: 11/293,575

(22) Filed: Dec. 2, 2005

(65) Prior Publication Data
US 2006/0142526 A1    Jun. 29, 2006

Related U.S. Application Data

(60) Provisional application No. 60/640,159, filed on Dec. 29, 2004.

(51) Int. Cl.
*G02B 1/04* (2006.01)
(52) U.S. Cl. .......... 523/106; 523/107; 528/28; 528/44; 528/45; 428/446; 428/447
(58) Field of Classification Search ............ 528/28, 528/44–45, 59; 523/106–107; 428/446–447
See application file for complete search history.

(56) References Cited

U.S. PATENT DOCUMENTS

| 3,408,429 A | 10/1968 | Wichterle |
| 3,660,545 A | 5/1972 | Wichterle |
| 4,113,224 A | 9/1978 | Clark et al. |
| 4,136,250 A | 1/1979 | Mueller et al. |
| 4,197,266 A | 4/1980 | Clark et al. |
| 4,605,712 A | 8/1986 | Mueller et al. |
| 5,034,461 A | 7/1991 | Lai et al. |
| 5,128,434 A * | 7/1992 | Lai ............ 528/65 |
| 5,260,000 A | 11/1993 | Nandu et al. |
| 5,271,875 A | 12/1993 | Appleton et al. |
| 5,449,729 A | 9/1995 | Lai |
| 5,760,100 A | 6/1998 | Nicolson et al. |
| 6,218,503 B1 | 4/2001 | Lai et al. |
| 7,423,074 B2 | 9/2008 | Lai et al. |
| 2003/0157141 A1 | 8/2003 | Lai et al. |
| 2006/0142525 A1 | 6/2006 | Lai et al. |

FOREIGN PATENT DOCUMENTS

EP    1043605 A1 *    10/2000

OTHER PUBLICATIONS

Yu-Chin Lai, "The Role of Bulky Polysiloxanylalkyl Methacrylates in Polyurethane-Polysiloxane Hydrogels", Journal of Applied Polymer Science, vol. 60, 1193-1199 (1996), John Wiley & Sons, Inc.
Yu-Chin Lai, "Novel Polyurethane-Silicone Hydrogels", Journal of Applied Polymer Science, vol. 56, 301-310 (1995), John Wiley & Sons, Inc.

* cited by examiner

*Primary Examiner*—Randy Gulakowski
*Assistant Examiner*—Olatunde S Ojurongbe
(74) *Attorney, Agent, or Firm*—Joseph Barrera

(57) ABSTRACT

A polysiloxane prepolymer that is useful for forming biomedical devices has the formula:

$$M(*Dii*PS)_x*Dii*M \qquad (I)$$

wherein:
each M is independently a polymerizable ethylenically unsaturated radical;
each Dii is independently a diradical residue of a diisocyanate;
each PS is independently a diradical residue of a polysiloxane-diol or a polysiloxane-diamine;
each * is independently —NH—CO—NH—, —NH—COO— or —OCO—NH—; and
x is at least 2.

24 Claims, No Drawings

POLYSILOXANE PREPOLYMERS FOR BIOMEDICAL DEVICES

This application claims priority under 35 USC 119(e) of prior provisional application Ser. No. 60/640,159, filed Dec. 29, 2004.

FIELD OF THE INVENTION

The present invention relates to polysiloxane prepolymers that are useful for forming biomedical devices, particularly ophthalmic devices including contact lenses, intraocular lenses and ophthalmic implants. This invention also relates to copolymers formed from the prepolymers, especially hydrogel copolymers.

BACKGROUND OF THE INVENTION

Hydrogels represent a desirable class of materials for the manufacture of various biomedical devices, including ophthalmic devices such as contact lenses. A hydrogel is a hydrated cross-linked polymeric system that contains water in an equilibrium state. Hydrogel lenses offer desirable biocompatibility and comfort. Silicone hydrogels are a known class of hydrogels and are characterized by the inclusion of a silicone-containing material. Typically, a silicone-containing monomer is copolymerized by free radical polymerization with a hydrophilic monomer, with either the silicone-containing monomer or the hydrophilic monomer functioning as a crosslinking agent (a crosslinker being defined as a monomer having multiple polymerizable functionalities) or a separate crosslinker may be employed. An advantage of silicone hydrogels over non-silicone hydrogels is that the silicone hydrogels typically have higher oxygen permeability due to the inclusion of the silicone-containing monomer.

Various polysiloxane-based prepolymers with urea or urethane linkages have been disclosed as potential silicone-containing monomers for silicone hydrogels. These various prepolymers may differ in their methods of preparation and in their physical characteristics/properties, and thus may exhibit divergent behavior when combined with other monomers for hydrogel copolymers.

One class of urethane- or urea-containing polysiloxane prepolymers involves endcapping polysiloxane-diol or polysiloxane-diamine with an ethylenically unsaturated monomer having an isocyanate group such as isocyanatoethyl methacrylate (IEM). For example, by reacting IEM with hydroxy-terminated polydimethylsiloxane, a prepolymer is formed. In general, this class of prepolymer exhibits similar compatibility with hydrophilic monomers as corresponding prepolymer without the urethane linkage, especially for higher molecular weight prepolymers. Also, in general, these prepolymers are liquid at room temperature. Examples of such prepolymers are found in U.S. Pat. No. 4,605,712 (Mueller et al.).

A second class of urethane-containing polysiloxane prepolymers employs a diisocyanate to create urethane linkages. In general, these prepolymers are prepared by reacting 2 moles of diisocyanate with a hydroxy-terminated polydimethylsiloxane, followed by end capping with 2-hydroxyethyl methacrylate (HEMA). This class exhibits slight improvement in compatibility with hydrophilic monomers such as N,N-dimethylacrylamide (DMA), depending on the molecular weight of polysiloxane. Also, in general, it is a liquid at room temperature. Examples of such prepolymers are found in U.S. Pat. No. 4,136,250 (Mueller et al.)

U.S. Pat. No. 5,034,461 (Lai et al.) discloses various polysiloxane-containing urethane or urea prepolymers. Generally, these prepolymers are derived from a short chain diol, a hydroxy-terminated polydimethylsiloxane and a diisocyanate, such that the structures resemble a segmented polyurethane elastomer; these prepolymers are endcapped with polymerizable ethylenically unsaturated radicals, such as HEMA reacted with isocyanate. These prepolymers may be copolymerized with a hydrophilic comonomer to form a silicone hydrogel copolymer that is useful as a contact lens material or other biomedical device applications. The preferred prepolymers of U.S. Pat. No. 5,034,461 are composed of soft polysiloxane segments (represented by A in the patent formulae) and strong hard segments (represented by *D*G*D* in the patent formulae), and are endcapped with polymerizable ethylenically unsaturated radicals.

The polysiloxane-containing prepolymers of this invention comprise more polar urethane or urea linkages per polysiloxane molecular weight, in comparison with U.S. Pat. No. 4,136,250 or U.S. Pat. No. 4,605,712, and the polysiloxane soft segment are linked to polymerizable groups though a diisocyanate which provides two urethane/urea linkages instead of one urethane/urea linkage in the case of U.S. Pat. No. 4,605,712, and are thus and are more compatible with hydrophilic monomers.

The polysiloxane-containing prepolymers of this invention comprise relatively weaker hard segments than the preferred prepolymers in U.S. Pat. No. 5,034,461. It has been found that this leads to several advantages. First, the present prepolymers tend to have a lower viscosity at room temperature; in fact they are fluid, making them easier to process in casting biomedical devices as compared to prepolymers with only strong hard segments such as those disclosed in U.S. Pat. No. 5,034,461. Second, this arrangement permits forming a prepolymer of higher silicone content, thereby permitting the formation of copolymers with higher oxygen permeabilities as compared to prepolymers disclosed in U.S. Pat. Nos. 4,136,250 or 4,605,712. In the prepolymers disclosed in these patents, the use of higher amounts of polysiloxane often leads to incompatibility when mixing monomer mixtures for casting. Third, in some cases, copolymers offering the higher oxygen permeabilities can be obtained without high modulus.

SUMMARY OF THE INVENTION

This invention provides a polysiloxane prepolymer that is useful for forming biomedical devices. The prepolymers are represented by the general formula:

$$M(*Dii*PS)_x*Dii*M \qquad (I)$$

wherein:

each M is independently a polymerizable ethylenically unsaturated radical;

each Dii is independently a diradical residue of a diisocyanate;

each PS is independently a diradical residue of a polysiloxane-diol or -diamine;

each * is independently —NH—CO—NH—, —NH—COO— or —OCO—NH—; and x is at least 2.

This invention further provides a copolymer that is the polymerization product of a monomeric mixture comprising the prepolymer and a comonomer. One preferred comonomer is a hydrophilic monomer, and another preferred comonomer is a monofunctional silicone-containing monomer. Preferred copolymers are hydrogels, that are the hydrated polymerization product of a monomeric mixture comprising the prepolymer and a hydrophilic comonomer. Especially preferred are hydrogel copolymers having a water content of at least 20 weight percent, a modulus no greater than 100 g/mm2, and/or an oxygen permeability of at least 100 barrers.

This invention further provides a biomedical device comprised of the copolymer, especially an ophthalmic device such as a contact lens or an intraocular lens.

DETAILED DESCRIPTION OF PREFERRED EMBODIMENTS

The prepolymers of this invention are represented by the formula:

$$M(*Dii*PS)_x*Dii*M \quad (I)$$

wherein:
each M is independently a polymerizable ethylenically unsaturated radical;
each Dii is independently a diradical residue of a diisocyanate;
each PS is independently a diradical residue of a polysiloxane-diol or a polysiloxane-diamine;
each * is independently —NH—CO—NH—, —NH—COO— or —OCO—NH—; and
x is at least 2.

Generally, the *Dii*PS blocks of formula (I) may be characterized as composed of relatively weak hard segments (represented by *Dii*) and soft segments (represented by PS).

The prepolymers include polysiloxane-containing soft segments, represented by PS in formula (I). More particularly, this polysiloxane-containing segment is derived from polysiloxanes endcapped with hydroxyl or amino radicals:

$$A-R-\underset{\underset{R'}{|}}{\overset{\overset{R'}{|}}{Si}}-(O-\underset{\underset{R'}{|}}{\overset{\overset{R'}{|}}{Si}})_a-O-R-A$$

wherein each A is a hydroxyl or amino radical;
each R is independently selected from an alkylene group having 1 to 10 carbon atoms wherein the carbon atoms may include ether, urethane or ureido linkages therebetween;
each R' is independently selected from hydrogen, monovalent hydrocarbon radicals or halogen substituted monovalent hydrocarbon radicals wherein the hydrocarbon radicals have 1 to 20 carbon atoms which may include ether linkages therebetween, and
a is at least 1.

Preferred R radicals are alkylene optionally substituted with ether radicals. Preferred R' radicals include: alkyl groups, phenyl groups, fluoro-substituted alkyl groups and alkenyl groups, optionally substituted ether groups. Especially preferred R' radicals include: alkyl, such as methyl; or fluoroalkyl optionally including ether linkages, such as —CH2-CH2-CH2-O—CH2- (CF2)z-H where z is 1 to 6.

Preferably, a is about 10 to about 100, more preferably about 15 to about 60. The Mn of PS ranges from 1000 to 8000, more preferably 2000 to 6000.

Various polysiloxane-diols and polysiloxane-diamines are commercially available. Additionally, representative syntheses of polysiloxanes are provided in the Examples.

The aforementioned polysiloxane-containing segments are linked via diisocyanates that react with hydroxyl- or amino-functionality of the polysiloxane-containing segments. Generally, any diisocyanate may be employed. These diisocyanates may be aliphatic or aromatic, and include alkyl, alkyl cycloalkyl, cycloalkyl, alkyl aromatic and aromatic diisocyanates preferably having 6 to 30 carbon atoms in the aliphatic or aromatic moiety. Specific examples include isophorone diisocyanate, hexamethylene-1,6- diisocyanate, 4,4'-dicyclohexylmethane diisocyanate, toluene diisocyanate, 4,4'-diphenyl diisocyanate, 4,4'-diphenylmethane diisocyanate, p-phenylene diisocyanate, 1,4-phenylene 4,4'-diphenyl diisocyanate, 1,3-bis-(4,4'-isocyanto methyl) cyclohexane, and cyclohexane diisocyanate.

In formula (I), x is at least two, more preferably at least three.

The prepolymers are endcapped at both ends with a polymerizable ethylenically unsaturated radical, represented by M in formula (I). Representative M radicals may be represented by the formula:

$$R_{24}\underset{R_{24}}{\overset{R_{23}}{\diagdown\diagup}}(CH_2)_b-(X)_c-(Q)_d-(Ar)_e-R_{25}-$$

wherein:
$R_{23}$ is hydrogen or methyl;
each $R_{24}$ is hydrogen, an alkyl radical having 1 to 6 carbon atoms, or a —CO —Y—$R_{26}$ radical
wherein Y is —0, —S— or —NH—;
$R_{25}$ is a divalent alkylene radical having 1 to 10 carbon atoms;
$R_{26}$ is an alkyl radical having 1 to 12 carbon atoms;
Q denotes —CO—, —OCO— or —COO—;
X denotes —0— or —NH—;
Ar denotes an aromatic radical having 6 to 30 carbon atoms; b is 0 to 6; c is 0 or 1; d is 0 or 1; and e is 0 or 1.

Suitable endcapping precursors, for forming the M radicals, include: hydroxy-terminated (meth)acrylates, such as 2-hydroxyethylmethacrylate, 2-hydroxyethylacrylate, and 3-hydroxypropylmethacrylate; and amino-terminated (meth) acrylates, such as t-butylaminoethylmethacrylate and aminoethylmethacrylate; and (meth)acrylic acid. (As used herein, the term "(meth)" denotes an optional methyl substituent. Thus, terms such as "(meth)acrylate" denotes either methacrylate or acrylate, and "(meth)acrylic acid" denotes either methacrylic acid or acrylic acid.)

A representative reaction scheme for forming the prepolymers is as follows. First, a diisocyanate is reacted with the polysiloxane-diol.

$$(n+1)OCN\text{-Dii-NCO}+nHO\text{—PS—OH}\rightarrow OCN\text{-}(Dii*PS)x*Dii\text{-NCO}$$

In this scheme, * designates a urethane radical —NH—COO— or —OCO—NH—. Generally, this reaction is conducted in the presence of a catalyst, such as dibutyl tin dilaurate and in a solvent, such as methylene chloride, and under reflux.

Finally, this product is endcapped with the polymerizable ethylenically unsaturated radical.

$$OCN\text{-}(Dii*PS)_n*Dii\text{-NCO}+2M\text{-OH}\rightarrow M(*Dii*PS)_n*Dii*M$$

In the above reaction scheme, the reaction of the polysiloxane-diol with the diisocyanate yields urethane radicals (—NH—COO— or —OCO—NH—). Alternatively, the reaction of poly-siloxane-diamines with diisocyanates would yield urea radicals (NH—CO—NH—). Other methods for forming urethane or urea polymers are known in the art, and representative syntheses are illustrated in the Examples.

The copolymers of this invention are formed by copolymerizing the prepolymers of this invention with one or more comonomers. Since the prepolymers are endcapped with polymerizable ethylenically unsaturated radicals, they are polymerizable by free radical polymerization. The monomeric mixtures employed in the invention include conventional lens-forming or device-forming monomers. (As used herein, the term "monomer" or "monomeric" and like terms denote relatively low molecular weight compounds that are polymerizable by free radical polymerization, as well as higher molecular weight compounds also referred to as "prepolymers", "macromonomers", and related terms.) For copolymers, the subject prepolymers are included in the monomer mixture at 5 to 95 weight percent, preferably 20 to 70 weight percent.

A hydrophilic comonomer may be included in the initial monomeric mixture containing the subject prepolymer, for example, if it is desired to obtain a more hydrophilic copolymer or to form a hydrogel copolymer. Representative hydrophilic comonomers include: unsaturated carboxylic acids, such as methacrylic and acrylic acids; (meth)acrylic substituted alcohols, such as 2-hydroxyethylmethacrylate, 2-hydroxyethylacrylate and glyceryl methacrylate; vinyl lactams, such as N-vinyl pyrrolidone; and (meth)acrylamides, such as methacrylamide and N,N-dimethylacrylamide. A hydrogel is a crosslinked polymeric system that can absorb and retain water in an equilibrium state. For hydrogel copolymers, at least one hydrophilic monomer is included in the monomer mixture at 20 to 60 weight percent, preferably 25 to 50 weight percent.

Another class of lens-forming or device-forming monomers is silicone-containing monomers. In other words, another silicone-containing comonomer, in addition to the subject prepolymer, may be included in the initial monomeric mixture, for example, if it is desired to obtain a copolymer with higher oxygen permeability.

One suitable class of silicone containing monomers include known bulky, monofunctional polysiloxanylalkyl monomers represented by Formula (VI):

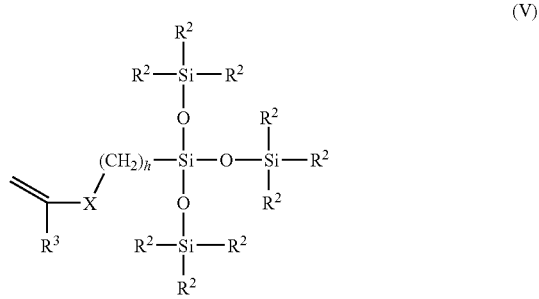

(V)

X denotes —COO—, —CONR$^4$—, —OCOO—, or —OCONR$^4$— where each where R$^4$ is H or lower alkyl; R$^3$ denotes hydrogen or methyl; h is 1 to 10; and each R$^2$ independently denotes a lower alkyl or halogenated alkyl radical, a phenyl radical or a radical of the formula —Si(R$^5$)$_3$ wherein each R$^5$ is independently a lower alkyl radical or a phenyl radical. Such bulky monomers specifically include methacryloxypropyl tris(trimethylsiloxy)silane (TRIS), pentamethyldisiloxanyl methylmethacrylate, tris(trimethylsiloxy) methacryloxy propylsilane, methyldi(trimethylsiloxy) methacryloxymethyl silane, 3-[tris(trimethylsiloxy)silyl] propyl vinyl carbamate, and 3-[tris(trimethylsiloxy)silyl] propyl vinyl carbonate.

Various difunctional and multifunctional silicone-containing monomers are known in the art and may be used as a comonomer if desired. The monomer mixtures may include the silicone monomer, in addition to the subject prepolymers, at 0 to 50 weight percent, preferably 5 to 30 weight percent when present.

In the case of silicone hydrogels, the monomer mixture includes a crosslinking monomer (a crosslinking monomer being defined as a monomer having multiple polymerizable functionalities). Since the subject prepolymers are endcapped at both ends with a polymerizable radical, the prepolymers will function as a crosslinker. Optionally, a supplemental crosslinking monomer may be added to the initial monomeric mixture. Representative crosslinking monomers include: divinylbenzene, allyl methacrylate, ethyleneglycol dimethacrylate, tetraethyleneglycol dimethacrylate, polyethyleneglycol dimethacrylate, vinyl carbonate derivatives of the glycol dimethacrylates, and 1-ethylene methacrylate, 2-vinylcarbonate. When a supplemental crosslinking agent is employed, this monomeric material may be included in the monomer mixture at 0.1 to 20 weight percent, more preferably at 0.2 to 10 weight percent.

In the case of intraocular lenses, the monomer mixtures may further include a monomer for increasing the refractive index of the resultant copolymer. Examples of such monomers are aromatic (meth) acrylates, such as phenyl (meth) acrylate, phenylethyl (meth)acrylate and benzyl (meth)acrylate.

An organic diluent may be included in the initial monomeric mixture. As used herein, the term "organic diluent" encompasses organic compounds that are substantially unreactive with the components in the initial mixture, and are often used to minimize incompatibility of the monomeric components in this mixture. Representative organic diluents include: monohydric alcohols, such as $C_2$-$C_{10}$ monohydric alcohols; diols such as ethylene glycol; polyols such as glycerin; ethers such as diethylene glycol monoethyl ether; ketones such as methyl ethyl ketone; esters such as methyl heptanoate; and hydrocarbons such as toluene.

In forming lenses or other biomedical devices, the monomeric mixtures may be charged to a mold, and then subjected to heat and/or light radiation, such as UV radiation, to effect curing, or free radical polymerization, of the monomer mixture in the mold. Various processes are known for curing a monomeric mixture in the production of contact lenses or other biomedical devices, including spincasting and static casting. Spincasting methods involve charging the monomer mixture to a mold, and spinning the mold in a controlled manner while exposing the monomer mixture to light. Static casting methods involve charging the monomer mixture between two mold sections forming a mold cavity providing a desired article shape, and curing the monomer mixture by exposure to heat and/or light. In the case of contact lenses, one mold section is shaped to form the anterior lens surface and the other mold section is shaped to form the posterior lens surface. If desired, curing of the monomeric mixture in the mold may be followed by a machining operation in order to provide a contact lens or article having a desired final configuration. Such methods are described in U.S. Pat. Nos.

3,408,429, 3,660,545, 4,113,224, 4,197,266, 5,271,875, and 5,260,000, the disclosures of which are incorporated herein by reference. Additionally, the monomer mixtures may be cast in the shape of rods or buttons, which are then lathe cut into a desired shape, for example, into a lens-shaped article.

One preferred application of the subject prepolymers is hydrogel contact lenses. For contact lens applications, it is preferred that the hydrogel copolymer, when fully hydrated, has a water content of at least 20 weight percent, as measured gravimetrically.

Also, in some cases, it is preferred that the hydrogel copolymer has a tensile modulus no greater than 100 g/mm$^2$. Modulus may be measured with an Instron (Model 4502) instrument according to ASTM D-1708a, where the hydrogel copolymer film sample is immersed in borate buffered saline. An appropriate size of the film sample is gauge length 22 mm and width 4.75 mm, where the sample further has ends forming a dogbone shape to accommodate gripping of the sample with clamps of the Instron instrument, and thickness of 200±50 microns.

It is preferred that the hydrogel copolymer has an oxygen permeability of at least 100 barrers, more preferably, at least 150 barrers. Oxygen permeability (also referred to as Dk) is determined by the following procedure. The oxygen permeability of silicone hydrogels are measured by the polarographic method (ANSI Z80.20-1998) using an O2 Permeometer Model 201T instrument (Createch, Albany, Calif. USA) having a probe containing a central, circular gold cathode at its end and a silver anode insulated from the cathode. Measurements are taken only on pre-inspected pinhole-free, flat silicone hydrogel film samples of three different center thicknesses ranging from 150 to 600 microns. Center thickness measurements of the film samples may be measured using a Rehder ET-1 electronic thickness gauge. Generally, the film samples have the shape of a circular disk. Measurements are taken with the film sample and probe immersed in a bath containing circulating phosphate buffered saline (PBS) equilibrated at 35° C.+/−0.2°. Prior to immersing the probe and film sample in the PBS bath, the film sample is placed and centered on the cathode premoistened with the equilibrated PBS, ensuring no air bubbles or excess PBS exists between the cathode and the film sample, and the film sample is then secured to the probe with a mounting cap, with the cathode portion of the probe contacting only the film sample. For silicone hydrogel films, it is frequently useful to employ a Teflon polymer membrane, e.g., having a circular disk shape, between the probe cathode and the film sample. In such cases, the Teflon membrane is first placed on the pre-moistened cathode, and then the film sample is placed on the Teflon membrane, ensuring no air bubbles or excess PBS exists beneath the Teflon membrane or film sample. Once measurements are collected, only data with correlation coefficient value (R$^2$) of 0.97 or higher should be entered into the calculation of Dk value. At least two Dk measurements per thickness, and meeting R$^2$ value, are obtained. Using known regression analyses, oxygen permeability (Dk) is calculated from the film samples having at least three different thicknesses. Any film samples hydrated with solutions other than PBS are first soaked in purified water and allowed to equilibrate for at least 24 hours, and then soaked in PHB and allowed to equilibrate for at least 12 hours. The instruments are regularly cleaned and regularly calibrated using RGP standards. Upper and lower limits are established by calculating a +/−8.8% of the Repository values established by William J. Benjamin, et al., *The Oxygen Permeability of Reference Materials*, Optom Vis Sci 7 (12s): 95 (1997), the disclosure of which is incorporated herein in its entirety:

| Material Name | Repository Values | Lower Limit | Upper Limit |
| --- | --- | --- | --- |
| Fluoroperm 30 | 26.2 | 24 | 29 |
| Menicon EX | 62.4 | 56 | 66 |
| Quantum II | 92.9 | 85 | 101 |

The following Examples illustrate various preferred embodiments of the invention.

EXAMPLE 1

Preparation of α,ω-bis(4-hydroxybutyl)polydimethylsiloxane (Mn about 3600)

The following were charged to a 2-L, three-neck round-bottom flask equipped with one reflux condenser: 51.26 grams of 1,3-bishydroxybutyl tetramethyldisiloxane; 863 grams of dimethoxydimethylsilane; 126 grams of distilled water; and 14.7 mL of concentrated hydrochloric acid. The mixture was heated at 60° C. for 1 hour. Methanol was then distilled off over a 5-hour period. Then, 279 ml distilled water and 279 mL concentrated HCl were added, and the contents were refluxed at 100° C. for 3 hours. The crude product was then separated from the aqueous layer. Then, 600 mL diethyl ether and 400 mL distilled water were added, and the solution was extracted twice with 400 mL sodium bicarbonate solution (0.5%) and then with distilled water until the washing had neutral pH. The product was then added slowly into a mixture of methanol/water (406 g/118 g). The bottom organic layer was separated, added with diethyl ether and dried with magnesium sulfate. Ether was then stripped under vacuum at room temperature and the residue was further stripped under vacuum (0.07-mm torr) at 80° C. The final product was recovered. The molecular weight (Mn) as determined by titration was 3598.

EXAMPLE 2

Preparation of α,ω-polydimethylsiloxane prepolymer using PDMS of Example 1

A dry 3-neck, 500-mL round-bottom flask was connected to a nitrogen inlet tube and a reflux condenser. The following were added to the flask all at once: isophorone diisocyanate (9.188 g, 41.333 mmol) (IPDI); α,ω-bis(4-hydroxybutyl)-polydimethylsiloxane from Example 1 (114.68 g, 31.873 mmol) (PDMS); dibutyl tin dilaurate (0.327 g); and 180 mL methylene chloride. The contents were refluxed. After overnight, the amount of isocyanate was determined to decrease to 22.0% by titration. The contents were cooled down to ambient temperature. 1,1'-bi-2- naphthol (0.0144 g) and 2-hydroxyethyl methacrylate (2.915 g, 22.399 mmol) were then added and the contents were stirred at ambient until isocyanate peak at 2267 cm$^{-1}$ disappeared from IR spectrum of the product. The solvent was then stripped under reduced pressure and the product was recovered (126 g). Theoretically, the prepolymer had 3 blocks containing of PDMS (x about 3).

EXAMPLE 3

Preparation of α,ω-polydimethylsiloxane prepolymer using PDMS of Example 1

The general procedure of Example 2 is followed, except that the molar ratio of PDMS to IPDI is 4:5, respectively.

149.6 g of prepolymer was recovered. Theoretically, the prepolymer had 4 blocks containing of PDMS (x about 4).

EXAMPLE 4

Preparation of α,ω-polydimethylsiloxane prepolymer using PDMS of Example 1

The general procedure of Example 2 is followed, except that the molar ratio of PDMS to IPDI is 5:6, respectively. 159.9 g of prepolymer was recovered. Theoretically, the prepolymer had 5 blocks containing of PDMS (x about 5).

EXAMPLES 5-14

Copolymers

Monomer mixtures were made by mixing the following components, listed in Tables 1 and 2 at amounts per weight: prepolymers of Examples 2, 3 and 4; methacryloxypropyl tris(trimethylsiloxy)silane (TRIS); N,N-dimethylacrylamide (DMA); 2-hydroxy ethyl methacrylate (HEMA); N-vinyl pyrrolidone (NVP); and/or methacryloxyethyl vinylcarbonate (HemaVC). Additionally, each monomer mixture included: 1,4-bis(2-methacrylamidoethylamino)anthraquinone as a tint (150 ppm); hexanol as a diluent (10 parts by weight); and Darocur™ UV initiator (Ciba Specialty Chemical, Ardsley N.Y.) (0.5 wt %).

The monomer mixtures were cast between silane-treated glass plates, and then cured under UV light for 1 hour. Each monomer mixture was cast between three sets of glass plates, each set of plates separated by Teflon™ polymer tapes of different thicknesses, such that three sets of film samples were obtained for each monomer mixture, with film thicknesses of about 200, 400 and 600 microns. The cured films were then extracted with isopropanol overnight, followed by hydration in deionized (DI) water, boiled in DI water for 4 hours and then saturated in borate buffered saline or phosphate buffered saline to give hydrogel films. The water content was measured gravimetrically. Mechanical tests were conducted in borate buffered saline according to ASTM D-1708a, discussed above. The oxygen permeabilities, reported in Dk (or barrer) units, were measured in phosphate buffered saline at 35° C., using acceptable films with three different thicknesses, as discussed above.

TABLE 1

| | Example | | | | |
|---|---|---|---|---|---|
| | 5 | 6 | 7 | 8 | 9 |
| Prepolymer Ex 2 | 65 | 65 | 60 | 65 | — |
| Prepolymer Ex 3 | — | — | — | — | 65 |
| Tris | 10 | 10 | 15 | 10 | 10 |
| DMA | 15 | 12 | 12 | 25 | 25 |
| NVP | 10 | 10 | 10 | — | — |
| Hema | — | 5 | 5 | — | — |
| HemaVC | 0.5 | 0.5 | 0.5 | — | — |
| % Water | 19.6 | 18.4 | 19.1 | 19.3 | 22.3 |
| Dk (barrer) | 224 | 300 | 224 | 219 | 257 |
| Modulus (g/mm²) | 187 | 180 | 143 | 152 | 102 |

TABLE 2

| | Example | | | | |
|---|---|---|---|---|---|
| | 10 | 11 | 12 | 13 | 14 |
| Prepolymer Ex 3 | 65 | 60 | — | — | — |
| Prepolymer Ex 4 | — | — | 65 | 65 | 60 |
| Tris | 10 | 15 | 10 | 10 | 15 |
| DMA | 12 | 12 | 25 | 12 | 15 |
| NVP | 10 | 10 | — | 5 | 10 |
| Hema | 5 | 5 | — | — | 2 |
| HemaVC | 0.5 | 0.5 | — | 0.5 | 0.5 |
| % Water | ND | 25.9 | ND | ND | 23.9 |
| Dk (barrer) | ND | ND | 171 | ND | 159 |
| Modulus (g/mm²) | ND | ND | 85 | ND | 79 |

The monomer mixtures prepared in Examples 10, 11 and 13 were cloudy so no films were cast. As the prepolymer in these examples were less polar, this suggests that prepolymers of lower polarity are less compatible with hydrophilic monomers. All hydrogel films were optically clear.

Having thus described various preferred embodiment of the invention, those skilled in the art will appreciate that various modifications, additions, and changes may be made thereto without departing from the spirit and scope of the invention, as set forth in the following claims.

We claim:

1. A hydrogel copolymer that is the hydrated polymerization product of a monomeric mixture comprising a prepolymer represented by the general formula:

$$M(*Dii*PS)_x*Dii*M \qquad (I)$$

wherein:
- each M is independently a polymerizable ethylenically unsaturated radical;
- each Dii is independently a diradical residue of a diisocyanate;
- each PS is independently a diradical residue of a polysiloxane-diol or a polysiloxane-diamine;
- each * is independently —NH—CO—NH—, —NH—COO— or OCO—NH—; and x is at least 2, and a hydrophilic comonomer, and wherein the hydrogel copolymer has sufficient optical quality and an oxygen permeability of at least 150 barrers.

2. The hydrogel copolymer of claim 1, wherein each Dii is a diradical residue of a diisocyanate selected from the group consisting of isophorone diisocyanate, hexamethylene-1,6-diisocyanate, 4,4'-dicyclohexylmethane diisocyanate, toluene diisocyanate, 4,4'-diphenyl diisocyanate, 4,4'-diphenylmethane diisocyanate, p-phenylene diisocyanate, 1,4-phenylene 4,4'-diphenyl diisocyanate, 1,3-bis-(4,4'-isocyanto methyl) cyclohexane, and cyclohexane diisocyanate.

3. The hydrogel copolymer of claim 1, wherein Mn of PS ranges from 1000 to 8000.

4. The hydrogel copolymer of claim 1, wherein x is at least 3.

5. The hydrogel copolymer of claim 1, wherein each M is independently a polymerizable ethylenically unsaturated radical of the formula:

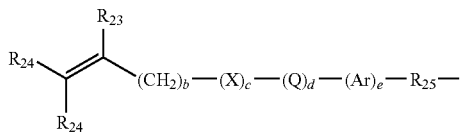

wherein:
$R_{23}$ is hydrogen or methyl;
each $R_{24}$ is hydrogen, an alkyl radical having 1 to 6 carbon atoms, or a —CO—Y—$R_{26}$ radical wherein Y is —O—, —S— or —NH—;
$R_{25}$ is a divalent alkylene radical having 1 to 10 carbon atoms;
$R_{26}$ is a alkyl radical having 1 to 12 carbon atoms;
Q is —CO—, —OCO— or —COO—;
X is —O— or —NH—;
Ar is an aromatic radical having 6 to 30 carbon atoms;
b is 0 to 6; c is 0 or 1; d is 0 or 1; and e is 0 or 1.

6. The hydrogel copolymer of claim 1, wherein:
each M is 2-ethylenemethacrylate;
each Dii is the diradical residue of isophorone diisocyanate;
each PS is a diradical residue of a polydimethylsiloxane-diol having Mn of at least 2000 to 3600; and
each * is —NH—COO— or —OCO—NH—.

7. The hydrogel copolymer of claim 1, wherein the hydrophilic monomer is selected from the group consisting of: unsaturated carboxylic acids; (meth)acrylic substituted alcohols; vinyl lactams; and (meth)acrylamides.

8. The hydrogel copolymer of claim 7, wherein the hydrophilic monomer is selected from the group consisting of: methacrylic acid; acrylic acid; 2-hydroxyethylmethacrylate; glyceryl methacrylate; N-vinyl pyrrolidone; methacrylamide; and N,N-dimethylacrylamide.

9. The hydrogel copolymer of claim 1, wherein the monomeric mixture further comprises a monofunctional silicone-containing monomer.

10. The hydrogel copolymer of claim 9, wherein the monomeric mixture further comprises methacryloxypropyl tris(trimethylsiloxy)silane.

11. The hydrogel copolymer of claim 1, having a water content of at least 20 weight percent.

12. The hydrogel copolymer of claim 1, having a modulus no greater than 100 g/mm$^2$.

13. The hydrogel copolymer of claim 1, having a water content of at least 20 weight percent, and a modulus no greater than 100 g/mm$^2$.

14. A biomedical device comprising a hydrogel copolymer of claim 1.

15. The hydrogel copolymer of claim 1, wherein x is at least 2 to about 5.

16. The hydrogel copolymer of claim 1 wherein each PS is a diradical residue of a polydimethylsiloxane-diol having Mn of at least 2000 to 3600.

17. An ophthalmic device comprising a hydrogel copolymer that is the hydrated polymerization product of a monomeric mixture comprising a prepolymer represented by the general formula:

$$M(*Dii*PS)_x*Dii*M \qquad (I)$$

wherein:
each M is independently a polymerizable ethylenically unsaturated radical;
each Dii is independently a diradical residue of a diisocyanate;
each PS is independently a diradical residue of a polysiloxane-diol or a polysiloxane-diamine;
each * is independently —NH—CO—NH—, —NH—COO— or OCO—NH—; and x is at least 2, and a hydrophilic comonomer, and wherein the hydrogel copolymer has sufficient optical quality and an oxygen permeability of at least 150 barrers, wherein the ophthalmic device is a contact lens or an intraocular lens.

18. The ophthalmic device of claim 17, wherein x is at least 2 to about 5.

19. The ophthalmic device of claim 17, wherein the monomeric mixture further comprises a monofunctional silicone-containing monomer.

20. The ophthalmic device of claim 17, wherein each PS is a diradical residue of a polydimethylsiloxane-diol having Mn of at least 2000 to 3600.

21. The ophthalmic device of claim 17, having a water content of at least 20 weight percent, a modulus no greater than 100 g/mm$^2$.

22. A contact lens comprising a hydrogel copolymer that is the hydrated polymerization product of a monomeric mixture comprising a prepolymer represented by the general formula:

$$M(*Dii*PS)_x*Dii*M \qquad (I)$$

wherein:
each M is independently a polymerizable ethylenically unsaturated radical;
each Dii is independently a diradical residue of a diisocyanate;
each PS is a diradical residue of a polydimethylsiloxane-diol having Mn of at least 2000 to 3600;
each * is independently —NH—CO—NH—, —NH—COO— or OCO—NH—; and x is at least 2, and a hydrophilic comonomer, and wherein the hydrogel copolymer has sufficient optical quality and an oxygen permeability of at least 100 barrers.

23. The contact lens of claim 22 having a water content of at least 20 weight percent, and a modulus no greater than 100 g/mm$^2$.

24. The contact lens of claim 22 wherein x is at least 2 to 5.

* * * * *